United States Patent [19]
Fejer et al.

[11] Patent Number: 5,235,404
[45] Date of Patent: Aug. 10, 1993

[54] INTERFEROMETRIC TECHNIQUE FOR MEASUREMENT OF NONRECIPROCAL OPTICAL EFFECTS IN A SAMPLE

[75] Inventors: Martin M. Fejer, Menlo Park; Aharon Kapitulnik, Palo Alto; Kenneth A. Fesler, Sunnyvale, all of Calif.

[73] Assignee: Board of Trustees, Leland Stanford Junior University, Stanford University, Stanford, Calif.

[21] Appl. No.: 722,338

[22] Filed: Jun. 27, 1991

[51] Int. Cl.⁵ .............................................. G01B 9/02
[52] U.S. Cl. ................................. 356/351; 356/345
[58] Field of Search ...................... 356/345, 350, 351

[56] References Cited

PUBLICATIONS

S. Spielman et al., "Test for Nonreciprocal Circular . . . ", The American Physical Society, Jul. 1990, pp. 123-126.
"Magnetooptics", McGraw-Hill Enc. of Science and Technology, 6th Ed., 1987, vol. 10, pp. 335-336.
"Hall Effect", McGraw-Hill Enc. of Science and Technology, 6th Ed., 1987, vol. 8, pp. 296-297.
U. Dürig et al., "Near-Field Optical-Scanning Microscopy", J. Appl. Phys., May 1988, vol. 59, No. 10, pp. 3318-3327.
A. A. Michelson et al., "The Effect of the Earth's Rotation . . . ," Nature, vol. 115, No. 2894, Apr. 1925.
R. White et al., "Long Range Order in Solids", Academic Press, 1979, pp. 317-323.
S. Spielman et al., "Test for Nonreciprocal Circular Birefringence in YBa$_2$Cu$_3$O$_7$ Thin Films as Evidence for Broken Time-Reversal Symmetry", *Physical Review Letters*, vol. 65, No. 1, Jul. 2, 1990.

*Primary Examiner*—Samuel A. Turner
*Attorney, Agent, or Firm*—Townsend and Townsend Khourie and Crew

[57] ABSTRACT

A method and apparatus for measuring nonreciprocal optical effects contemplates directing two circularly polarized optical beams having a known phase relation to each other at a sample, and detecting the difference in phase between the two beams after they have encountered the sample. In a transmission measurement the two circularly polarized beams have the same handedness, but pass through the sample in opposite directions. In a reflection measurement, the two circularly polarized beams have opposite handedness, but encounter the sample in the same direction. In a particular embodiment of the invention a linearly polarized beam is introduced into a Sagnac interferometer and split into two linearly polarized beams which are ultimately recombined.

31 Claims, 6 Drawing Sheets

INTERFEROMETRIC TECHNIQUE FOR MEASUREMENT OF NONRECIPROCAL OPTICAL EFFECTS IN A SAMPLE

BACKGROUND OF THE INVENTION

The present invention relates generally to optical measurements and more specifically to interferometric and microscopic techniques for measurement of small phase shifts indicative of nonreciprocal optical effects.

Magneto-optic phenomena such as the Faraday and Kerr effects have been well-known for over a century. For example, controlled Faraday rotation has long been used in optical and microwave instruments where it is desired to rotate the plane of polarization by a known amount (say 45° or about 0.8 radian). Similarly the Kerr effect has been exploited in the field of magneto-optic memories, and shows promise. In this context, the phase shifts tend to be on the order of many milliradians.

More recently, the Kerr effect has been used to measure the magnetic characteristics of monolayers and submonolayers of selected isotropic magnetic materials. Sensitivities on the order of 5-10 $\mu$rad have been reported using crossed polarizers, but in the context of high applied magnetic fields (say on the order of a kilogauss) and long data acquisition times.

SUMMARY OF THE INVENTION

The present invention provides a method and apparatus for measuring relative phase shifts arising from nonreciprocal optical effects at the level of a few microradians or less, optionally with a spatial resolution as low as the 20-nm range. The technique is inherently insensitive to reciprocal effects such as birefringence, dichroism, and similar effects that would tend to mask small nonreciprocal effects in other measurement schemes.

In brief, the invention contemplates directing two circularly polarized optical beams having a definite (but not necessarily known) phase relationship to each other at a sample, and using interferometric techniques to detect the change in the phase relationship between the two beams after they have encountered the sample. Such relative phase changes represent the nonreciprocal effects sought to be measured, and produce a change in the interferometer signal intensity. The present invention subjects the beams to a nonreciprocal timevarying bias to distinguish these changes in signal intensity (due to such relative phase shifts) from other possible changes in signal intensity. This may be done by using a phase modulator.

In a first type of transmission measurement, the two circularly polarized beams have the same handedness, but pass through the sample in opposite directions. In a reflection measurement and in a second type of transmission measurement, the two circularly polarized beams have opposite handedness, but encounter the sample in the same direction.

In specific embodiments of the invention, a linearly polarized beam is split into two linearly polarized beams, which are ultimately recombined. Each beam is converted to a circularly polarized beam prior to encountering the sample, and is converted back to a linearly polarized beam after encountering the sample. Both beams travel the same path prior to recombination. This may be done in an optical fiber Sagnac interferometer.

For the first type of transmission measurement, conversion from linear polarization to circular, and back again is effected by first and second quarter-wave plates, one on each side of the sample. Each beam passes through each plate and the sample once. For the reflection measurement and the second type of transmission measurement, there is only a single quarter-wave plate, through which each beam passes twice. In the second type of transmission measurement, each beam passes through the sample twice.

The present invention can be implemented using near field microscopy techniques that provide resolution in the range of tens of nanometers. In a preferred embodiment, the transverse extent of the circularly polarized beam at the sample is limited by passing the beam through a tapered fiber, the small end of which is very near the sample.

A further understanding of the nature and the advantages of the present invention may be realized with reference to the remaining portions of the specification and drawings.

DESCRIPTION OF SPECIFIC EMBODIMENTS

Figure 1A:
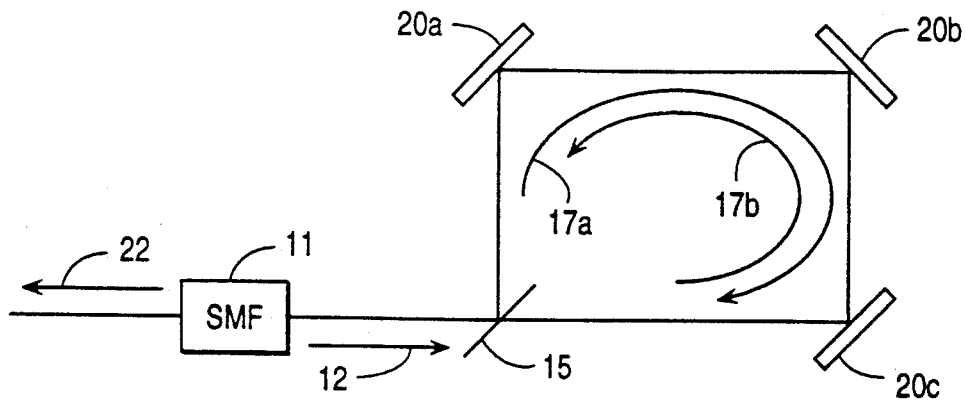
FIG. 1A is a schematic view showing the optical layout of a prior art Sagnac interferometer.
Figure 1B:
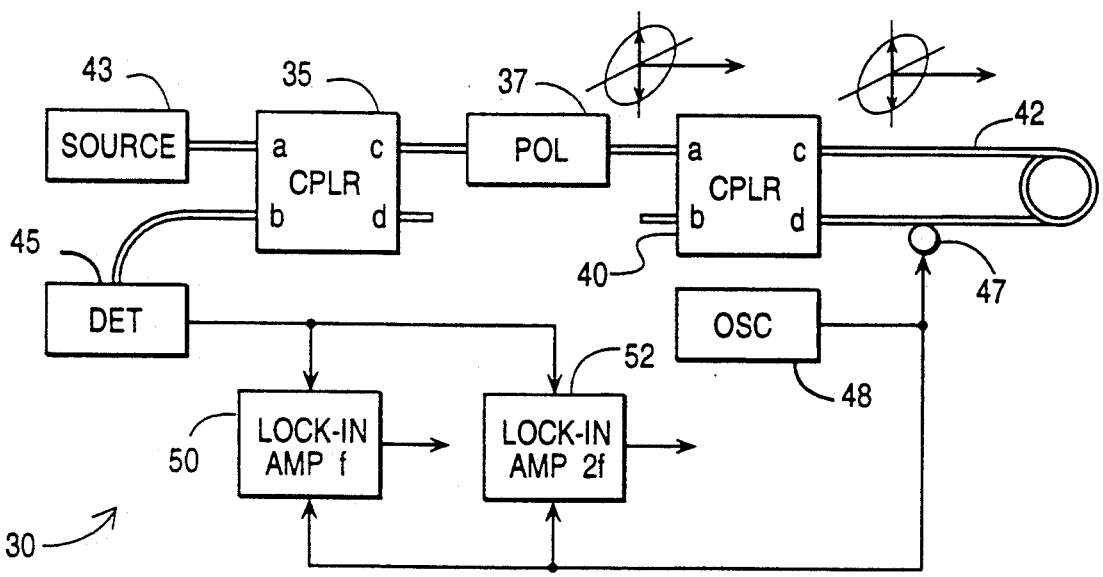
FIG. 1B is a system diagram illustrating a prior art Sagnac interferometer as embodied in a fiber gyroscope.

Sagnac Interferometer Overview (FIGS. 1A and 1B)

FIG. 1A is an optical schematic illustrating the basic configuration of a Sagnac interferometer 10. An input beam encounters a single-mode filter 11 and emerges as a beam 12. Beam 12 encounters a beam splitter 15, and is split into reflected and transmitted beam components 17a and 17b, referred to simply as beams 17a and 17b. Beam 17a encounters a series of reflectors 20a, 20b, and 20c, which direct the beam back to beam splitter 15. Beam 17b encounters the reflectors in the reverse order. Beams 17a and 17b combine at the beam splitter, pass through single-mode filter 11, and emerge to form an output beam 22. Beam 12 and beam 22 each consist of a single spatial and polarization mode.

Since the counterpropagating beams 17a and 17b are traveling over an identical optical path (including phase shifts at the beam splitter and reflectors), they interfere constructively, and are directed through the beam splitter along the path of the incoming beam. To the extent that a relative phase shift has occurred, some destructive interference will occur, and part of the output beam will be coupled into the other port of the beam splitter. If the interferometer is subjected to a mechanical rotation, the beams will undergo a relative phase shift proportional to the component of angular velocity perpendicular to the plane of the interferometer, and the intensity of output beam 22 will be decreased.

FIG. 1B is a system schematic showing a particular fiber-optic implementation of the Sagnac interferometer as used in a prior art fiber-optic gyroscope 30. The optical train includes a directional coupler 35 having ports 35a–d, a polarizer 37, a directional coupler 40 having ports 40a–d, and a loop 42 of polarization-preserving single-mode fiber. Light from a source 43 enters port 35a, whereupon a portion of it passes through port 35c to polarizer 37 and the rest is lost, primarily through port 35d. The polarized beam enters port 40a and is split into first and second beams at ports 40c and 40d, which beams enter the opposite ends of fiber loop 42. The counterpropagating beams enter ports 40d and 40c and are recombined. To the extent that no relative phase shift has occurred, they constructively interfere and enter port 40a. The light passes through polarizer 37 and enters port 35c. A portion of the light passes back to source 43 through port 35a and another portion passes through port 35b to a detector 45.

A phase modulator 47 is coupled to the fiber loop and is driven by a reference oscillator 48. In order for the phase modulation to be effective, the transducer is located away from the center of the loop. The reference oscillator also provides reference signals to first and second lock-in amplifiers 50 and 52, which measure components of the detector signal at the reference oscillator frequency and at twice the reference oscillator frequency. As will be described in detail below, the ratio of the two components provides the desired relative phase information.

A first embodiment of the interferometer uses a 1060-nm neodymium-doped glass laser as a source. The interferometer loop comprises 1 km of polarization-preserving single-mode (at 1060 nm) optical fiber wound on a 20-cm-diameter spool. The phase modulator is a piezoelectric hoop transducer, around which is wrapped about 10 m of the fiber, and which is driven at 100 KHz. The detector is a silicon p-i-n photodiode and the 100-KHz and 200-KHz components of the output corresponding to the first and second harmonics of the reference are measured with lock-in amplifiers with a time constant of 1 to 10 seconds.

A second embodiment of the interferometer uses a 670-nm laser diode as a source. Whereas the first embodiment of the interferometer was originally optimized as a gyroscope, the second embodiment was developed specifically in connection with the invention, and is thus more suited for the study of magneto-optic materials. The loop length is 20 m rather than 1 km, thereby reducing the effects of thermal and acoustic fluctuations. As in the first embodiment, the fiber is polarization-preserving and single-mode. However, the proportionately higher phase modulation frequency (the optimum frequency scales inversely with the length of the loop) requires an electro-optic modulator, which is inserted into the path, rather than the simpler piezoelectric fiber stretcher used in the first embodiment. The second embodiment is currently in development and has about 2 $\mu$rad of noise in a 1-Hz bandwidth. In addition, it is characterized by an offset of 0–20 $\mu$rad, apparently due to imperfections in the phase modulator. The offset can be nulled by slight adjustments in the optics which guide the light through the modulator. Alignment of the sample and its associated optics does not affect the offset.

It will be appreciated that the polarizer and the polarization-preserving single-mode fiber act as a single-mode filter. Any light that is scattered into a different spatial mode rapidly leaks out of the fiber while any light that is converted to a different polarization is rejected by the polarizer before reaching the detector.

As will be described in more detail below, in the present invention, the first and second linearly polarized beams are converted to respective first and second circularly polarized beams before encountering the sample and back to linearly polarized beams after encountering the sample. The linearly polarized beams may at some point become slightly elliptical, or the circularly polarized beams may not be perfectly circularly polarized. However, it is still meaningful to describe the invention in terms of linearly and circularly polarized beams, even through slight departures may be present at some points in the optical train.

Figure 2:
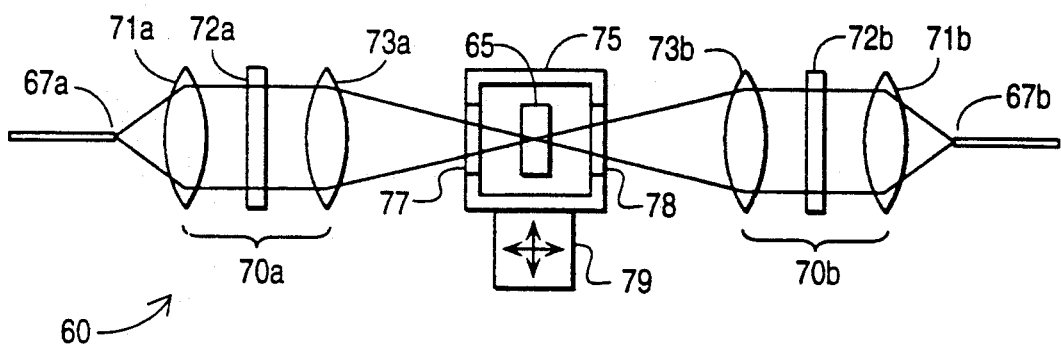
FIG. 2 is an optical schematic illustrating the bulk optics inserted into the optical path of the interferometer for performing a first type of transmission measurement according to the present invention.

Optics for a First Type of Transmission Measurement (FIG. 2)

FIG. 2 is an optical schematic illustrating a bulk optics section 60 that is inserted into the optical path of the interferometer to perform a first type of transmission measurement in a sample 65. A break is formed in fiber loop 42, providing first and second fiber ends 67a and 67b. This should be away from the midpoint of the path to reduce adverse effects of coherent scattering.

The bulk optics comprises a pair of subassemblies 70a and 70b, which include respective first lenses 71a and 71b, respective quarter-wave plates (QWPs) 72a and 72b, and respective second lenses 73a and 73b. Sample 65 is located within a cryostat 75 having optical windows 77 and 78. The cryostat is mounted on an x-y-z stage 79 to permit scanning multiple samples and multiple points on a given sample.

The linearly polarized light emerging from fiber end 67a is collimated by lens 71a, converted to right circularly polarized light by quarter-wave plate 72a, and focused on the sample by lens 73a. A typical 1/$e^2$ beam diameter is about 15 $\mu$ with a depth of focus of ~0.5 mm. The light diverges from the sample and encounters subassembly 70b where it is collimated by lens 73b, converted to linearly polarized light by QWP 72b, and focused on fiber end 67b. Light emerging from fiber end 67b follows the reverse path and is ultimately focused on fiber end 67a. Thus in each case, the linearly polarized light is converted to right circularly polarized light prior to encountering the sample and is then converted back to light of the original linear polarization after leaving the sample.

Figure 3:
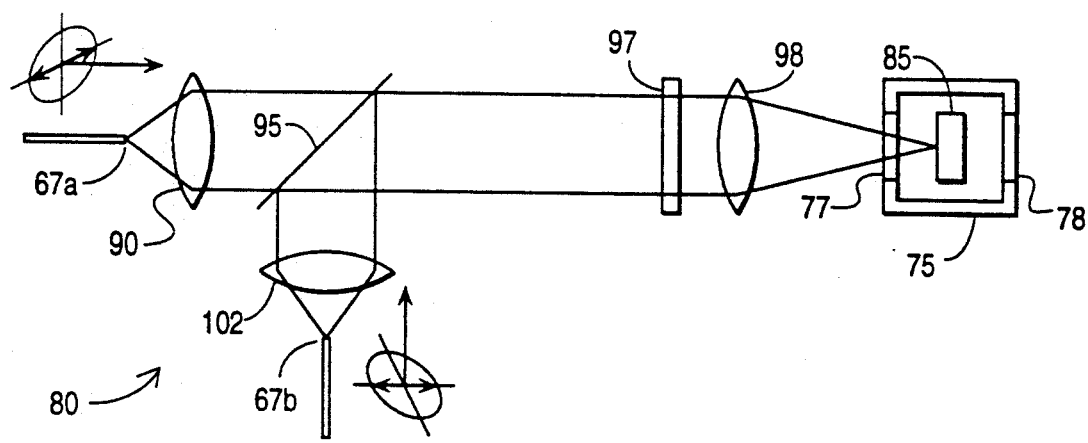
FIG. 3 is an optical schematic of bulk optics inserted into the path for performing a reflection measurement according to the present invention.
Figure 4:
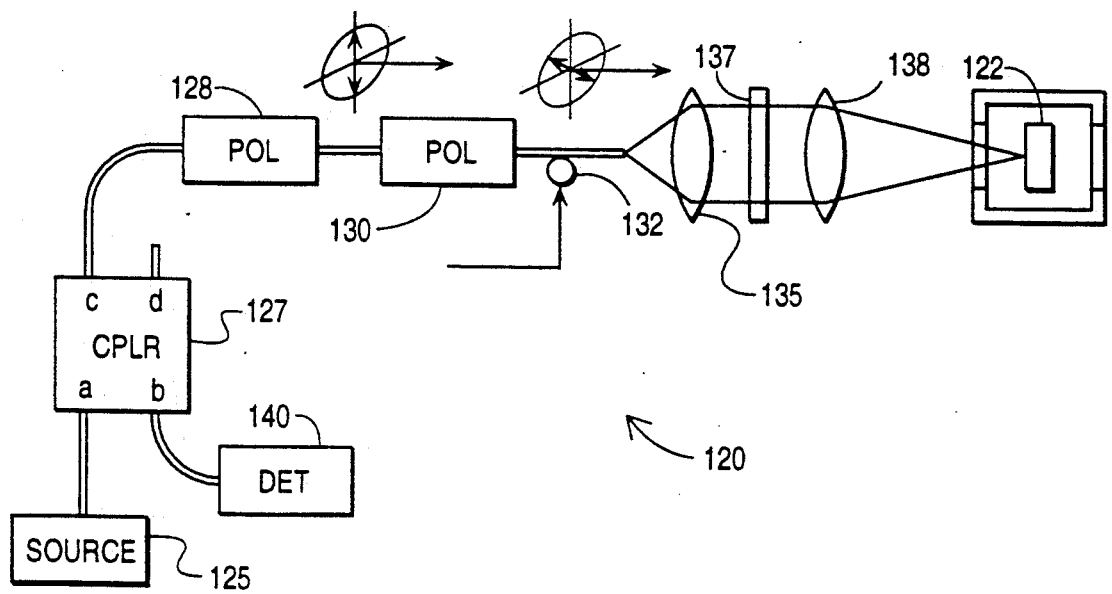
FIG. 4 is an optical schematic of an alternative embodiment of the invention for performing a reflection measurement.

Optics for Reflection Measurement (FIGS. 3 and 4)

FIG. 3 is an optical schematic illustrating a bulk optics section 80 that is inserted into the path to perform a reflection measurement on a sample 85. As in the case above, light emerging from fiber end 67a encounters the sample and then enters fiber end 67b while light emerging from fiber end 67b encounters the sample and enters fiber end 67a. This embodiment differs in that the beam emerging from fiber end 67a is linearly polarized in a plane perpendicular to the plane of the drawing while the beam emerging from fiber end 67b is linearly polarized in the plane of the drawing. Since the beams had the same polarization when they were input to fiber loop 42, the change in polarization needs to be effected by any convenient mechanism, such as twisting the fiber on one side of the break by 90° or placing a 90° reciprocal rotator (e.g., a crystal quartz plate) in the path.

The light emerging from fiber end 67a is collimated by a lens 90 and encounters a polarization-sensitive beam splitter 95. The light passes through beam splitter 95, is converted to right circularly polarized light by a QWP 97 and is focused on sample 85 by a lens 98. The light is reflected, which changes its circular polarization from right-handed to left-handed. The light is collimated by lens 98, and converted by QWP 97 to linearly polarized light with its plane of polarization in the plane of the drawing. Accordingly, it is reflected at beam splitter 95, and is collimated by a lens 102 prior to entering fiber end 67b.

In a similar fashion, the light emerging from fiber end 67b, which light has its plane of polarization in the plane of the figure, is collimated by lens 102, reflected at beam splitter 95, converted to left circularly polarized light by QWP 97, and, focused on the sample by lens 98. On reflection, the left circularly polarized light is converted to right circularly polarized light, so that when it is collimated by lens 98 and passes through QWP 97, it is converted to linearly polarized light with its plane of polarization perpendicular to the plane of the figure. The light therefore passes through the beam splitter, and is focused on fiber end 67a.

FIG. 4 is an optical schematic of alternative apparatus 120 for performing a reflection measurement on a sample 122. This embodiment differs from the embodiment FIG. 3 in that it uses a single fiber strand rather than a loop. Light from a source 125 is passed through a directional coupler 127 and through a polarizer 128 which provides linear polarization along one of the principal axes of the fiber (perpendicular to the fiber direction and assumed to be in the plane of the drawing). The linearly polarized light passes through a second polarizer 130 whose plane of polarization is at 45° to the principal axes of the fiber (also 45° to the plane of the drawing), whereupon the light emerges having been decomposed into components having their respective planes of polarization parallel and perpendicular to the plane of drawing. Polarizer 128 is optional, and polarizer 130 can be at any non-zero angle to the principal axis, but 45° provides maximum intensity.

A phase modulator 132 is coupled to the fiber and is driven to provide phase modulation. Since both components are being modulated at the same time, proper operation requires that the magnitudes of the two modulations differ. A lithium tantalate bulk electro-optic modulator (such as that used in the second interferometer embodiment) has this property, and can therefore be used here.

The light emerging from the end of the fiber is collimated by a lens 135, passes through a QWP 137, and is focused on the sample by a lens 138. QWP 137 converts the two linearly polarized components to right and left circularly polarized light before they encounter the sample. As described above, upon reflection, the handedness of the light is changed, and the beams propagate back through the optical train to directional coupler 127 and a detector 140. As above, a relative phase shift between the two components signifies a nonreciprocal effect.

Figure 5:
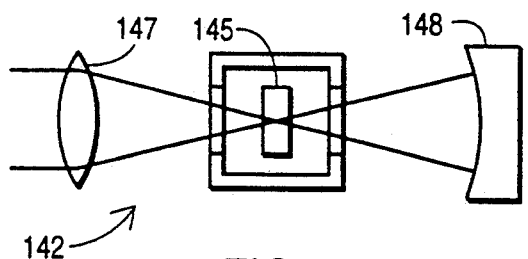
FIG. 5 is an optical schematic of optics for performing a second type of transmission measurement.

Optics for a Second Type of Transmission Measurement (FIG. 5)

FIG. 5 is an optical schematic of apparatus 142 that can be used to modify the apparatus of FIG. 3 or FIG. 4 to render it suitable for performing a transmission measurement on a sample 145. Circularly polarized light (corresponding to both the circularly polarized beams, which have opposite handedness) is focused on the sample by a lens 147 (which could correspond to lens 98 in FIG. 3 or lens 138 in FIG. 4) and passes through the sample. Light emerging from the sample encounters and is reflected by a concave mirror 148, and the reflected light re-enters the sample. Thus each beam passes through the sample twice.

The concave lens is located so that it focuses the light where it had been focused by lens 147. Thus the reflected light is collimated by lens 147 and travels the reverse path as in the reflection measurement. Reflection at the mirror causes each beam to change its handedness and typically to undergo a phase shift. However this is reciprocal and so adds no relative phase shift between the beams.

Figure 6:
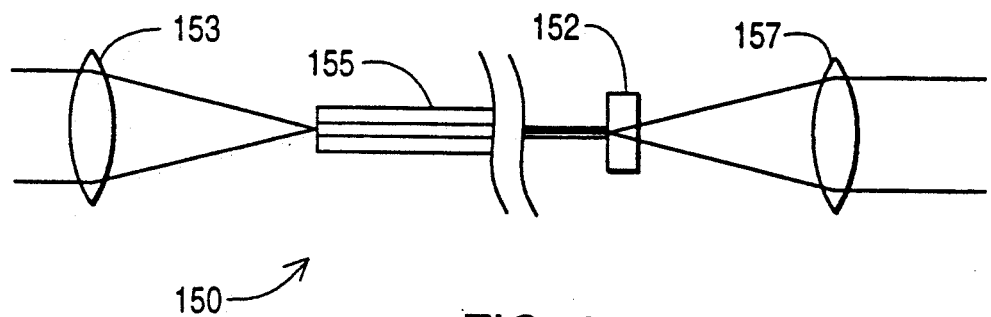
FIG. 6 is an optical schematic illustrating the optics for the first type of transmission measurement utilizing near field microscopy techniques.
Figure 7:
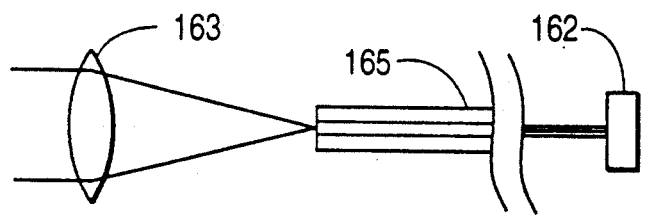
FIG. 7 is an optical schematic illustrating the optics for a reflection measurement utilizing near field microscopy techniques.
Figure 8:
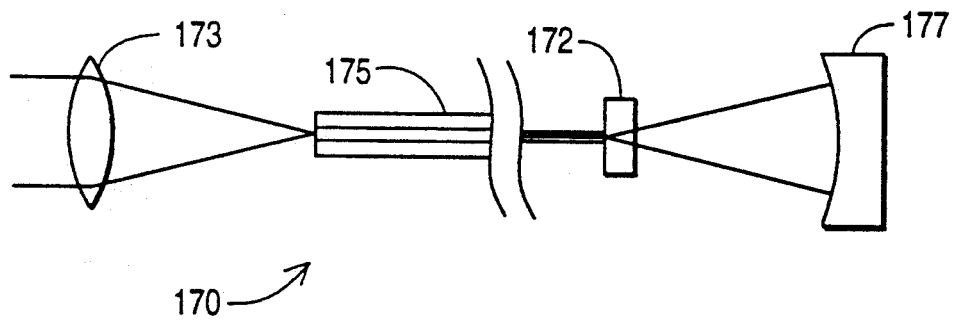
FIG. 8 is an optical schematic illustrating the optics for the second type of transmission measurement utilizing near field microscopy techniques.

Near Field Microscopy Technique (FIGS. 6-8)

The various embodiments described above, in combination with the ability to translate the sample, constitute a conventional scanning microscope. Although a 15-$\mu$ beam spot was used, a diffraction-limited beam spot (on the order of 1 $\mu$) could be obtained with suitable optics. According to a further aspect of the invention, near field microscopy techniques are used to provide a spatial resolution much smaller than even diffraction limited optics.

In brief, the transverse extent of the illuminated portion of the sample is limited to a dimension much less than the wavelength of the illuminating radiation. This can be particularly useful for materials (such as magnetic materials) which break into domains. Since the nonreciprocal effect averages to zero over many domains, the phase shifts must be determined from the distribution width. The ultimate sensitivity would be achieved by probing a single domain which can be achieved or at least approached by going to a much smaller beam spot. With such a small beam spot, it would also be possible to create images of magnetic and other materials' structures.

FIG. 6 is an optical schematic of apparatus 150 that uses a near field microscopy technique in connection with performing the first type of transmission measurement on a sample 152. This apparatus represents a modification or enhancement to the optics shown in FIG. 2. Specifically, the first circularly polarized beam is focused by a lens 153 (which could correspond to lens 73a in FIG. 2) on the core at the large end of a tapered optical fiber 155. The fiber is shown with greatly exaggerated transverse dimensions. Fiber 155 is drawn to a very fine taper coated with metal such that the outer diameter of the fiber at the small end is a few to several tens of nanometers (say 20-50 nm). This represents a transverse dimension an order of magnitude or more smaller than the wavelength of the light.

The small amount of light emerging from the small end of fiber 155 passes through the sample and a small portion is collected by a lens 157 (which could correspond to lens 73b in FIG. 2, but is preferably a microscope objective). The second circularly polarized beam (traveling the reverse direction) is focused by lens 157 to a beam spot that is microns in diameter and a small portion enters the small end of the fiber.

FIG. 7 is an optical schematic of apparatus 160 that uses the same near field microscopy technique in connection with performing a reflection measurement on a sample 162. Both the circularly polarized beams are focused by a lens 163 (which could correspond to lens 98 in FIG. 3 or lens 138 in FIG. 4) on the core of a tapered optical fiber 165. Light emerging from the tapered tip encounters the sample, is reflected by the sample, and a portion of the reflected light re-enters the fiber.

FIG. 8 is an optical schematic of apparatus 170 that uses the same near field microscopy technique in connection with performing the second type of transmission measurement on a sample 172. Both the circularly polarized beams are focused by a lens 173 (which could correspond to lens 147 in FIG. 5 on the core of a tapered optical fiber 175. The small amount of light emerging from the small end of fiber 175 passes through the sample and a small portion is reflected by a concave mirror 177 (which could correspond to mirror 148 in FIG. 5). The reflected light is focused by mirror 177 to a beam spot that is microns in diameter and a small portion enters the small end of the fiber.

Tapering the fiber is in some sense equivalent to focusing the light on a minute pinhole aperture. Where a pinhole aperture is on the order of or larger than the wavelength of the light, it limits the transmission generally in proportion to ratio of the aperture area to the beam spot area. However, when the aperture diameter is significantly less than a wavelength, the transmission is limited by much more than the ratio of the areas.

A consequence of using the tapered fiber (for both transmission and reflection) is that most of the light entering the large end of the fiber is reflected back before reaching the small end. This light represents background, which is far greater than the amount of light reaching the sample, which light will carry the signal information. Thus, it would normally be extremely difficult or even impossible to recover the signal from the overwhelming background. However, the background reflection can be expected to contain the result of reciprocal effects only. Accordingly, the apparatus of the present invention, which is inherently insensitive to reciprocal effects is able to detect the presence of any nonreciprocal effects from the sample, notwithstanding the presence of the background.

Apparatus Characteristics

The purpose of the apparatus is to measure nonreciprocal optical effects while rejecting reciprocal effects. The two circularly polarized beams, when they encounter the sample, have a definite phase relationship to each other. This relationship is determined by the portions of the path over which the beams had traveled since being split from a single linearly polarized beam. The particular relationship is, as a practical matter, not easily determinable, but this is not significant. Since the beams ultimately travel the same path prior to recombination, any relative phase shifts due to reciprocal effects are, in effect, undone after both beams have traversed the entire path. The crucial exception to this is relative phase shifts due to nonreciprocal effects.

Accordingly, the apparatus provides a measurement of the relative phase shifts that the two beams undergo when they are circularly polarized and encounter the sample (assuming no other nonreciprocal effects). While the reciprocal effects cannot contribute to the relative phase shift, they can couple energy from the desired mode to modes that are rejected by the single-mode filter, and thus can reduce the detected power. Thus, the apparatus must be able to measure the relative phase shift in the presence of possible variations in the power in the desired modes. The phase modulator provides a time-varying nonreciprocal bias that distinguishes such variations in power (due to such coupling of energy into other modes that are ultimately rejected by the single-mode filter) from variations arising from a relative phase shift due to nonreciprocal optical effects.

The phase modulator provides first and second harmonic signals, the first being representative of the nonreciprocal phase shift and the second providing an overall scale factor (a measure of the system throughput). Reciprocal effects may operate to scale both harmonic signals proportionately downwardly but cannot create a first harmonic signal in the absence of a nonreciprocal effect. Specifically, the first harmonic is $k_1 I_0 \sin(\Delta\Phi)$, which for small nonreciprocal signals (or low mechanical rotation rate) is approximately $k_1 I_0 \Delta\Phi$. The second harmonic is $k_2 I_0 \cos(\Delta\Phi)$, which for small signals is approximately $k_2 I_0$. $I_0$ is the optical power and $k_1$ and $k_2$ are determined by the system parameters.

For transmission through a sample as shown in FIG. 2, the apparatus measures a phase shift given by:

$$\Delta\Phi = 2\pi L(n_+ - n_-)/\lambda$$

where L is the sample thickness and $n_+$ and $n_-$ are the real parts of the indices of refraction for circularly polarized light of the same handedness propagating in opposite directions through the sample. Equivalently $n_+$ and $n_-$ could refer to the real parts of the indices of refraction for right and left circularly polarized light propagating in the same direction, in which case $\Delta\Phi$ is related to the Faraday rotation angle $\theta$ by $\Delta\Phi = 2\theta$. For transmission through the sample as shown in FIG. 5, the measured phase shift is twice as large since the light passes through the sample twice.

For reflection off a sample, the apparatus measures a phase shift corresponding to the polar Kerr effect. This is the difference in phase shift that right and left circularly polarized light undergo upon reflection. If the apparatus were modified to accommodate other than normal incidence, the apparatus would also measure phase shifts corresponding to the transverse and longitudinal Kerr effects.

The nature of the apparatus is that it is insensitive to reciprocal effects, and furthermore is insensitive to minor misalignment and imperfections in the components. For example, a minor misalignment of the quarter-wave plates, which is a reciprocal effect, while losing signal by coupling light into the wrong polarization mode of the fiber (which is eventually rejected by polarizer 37) cannot cause a change in the relative phase. Moreover, in the first type of transmission measurement, since both beams have the same handedness, the apparatus is insensitive to an optically active material (i.e., a chiral molecule like sucrose) whose index depends on the handedness of the light, but not the direction of propagation. The same is true in the second type of transmission measurement, since each beam passes through the sample as both right and left circularly polarized light. Furthermore, a linearly birefringent material, while coupling some light into the other polarization mode, would still behave identically in both propagation directions, and the beams would again emerge with no relative phase shift.

However, in the case of the Faraday effect, the refractive index of the material depends not only on the handedness of the light, but also on the direction of propagation. Thus, the apparatus is inherently sensitive only to nonreciprocal process like the Faraday effect.

It should be appreciated that various imperfections can combine to produce spurious effects. This has been thoroughly studied in the field of fiber-optic gyroscopes, and the considerations and remedies are well understood. For example, the quality of the polarizer is particularly important since various imperfections can act as polarization scatterers.

Figure 9A:
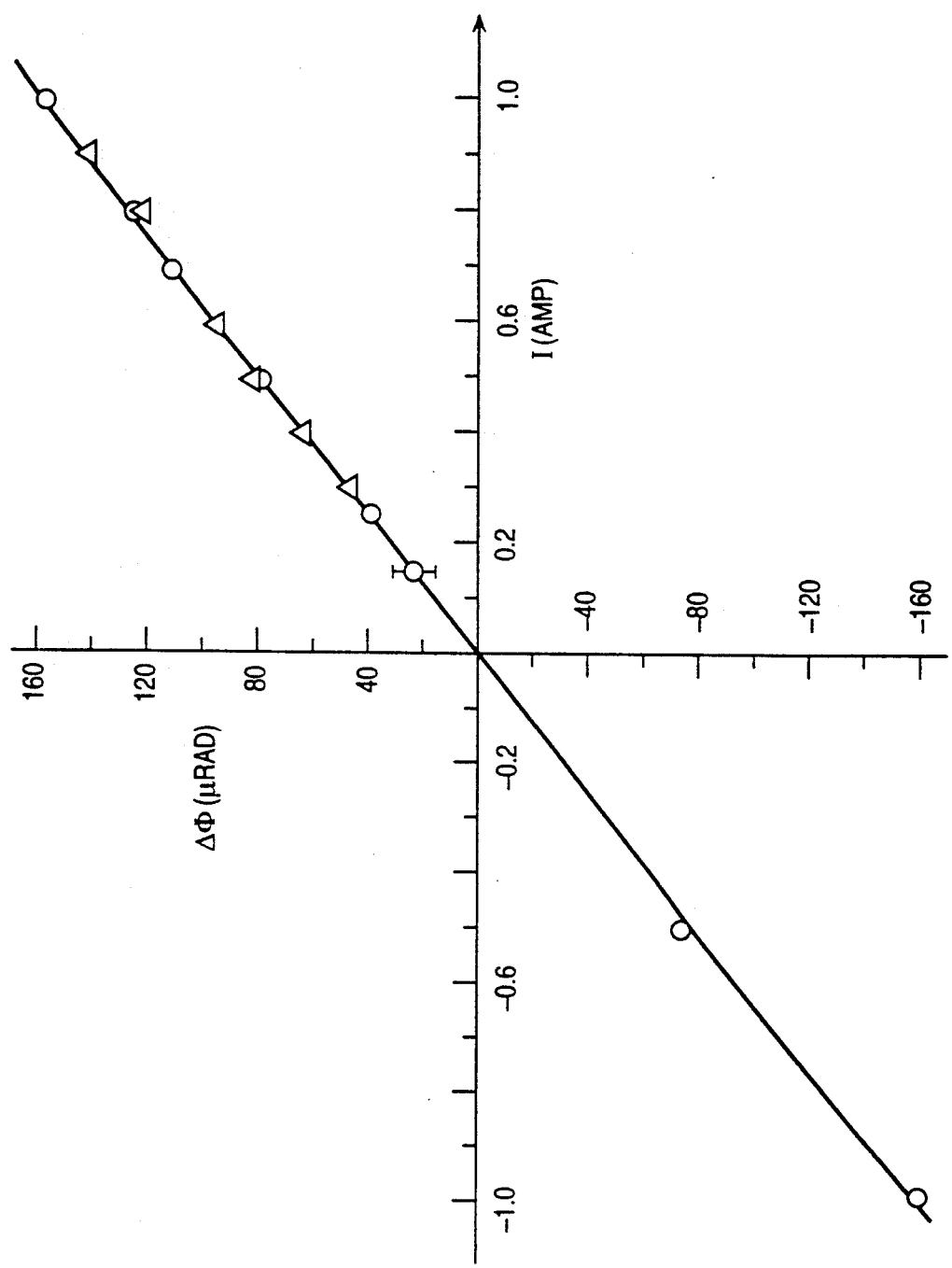
FIGS. 9A-C are experimental plots showing phase shifts measured using materials exhibiting Faraday and Kerr effects.
Figure 9B:
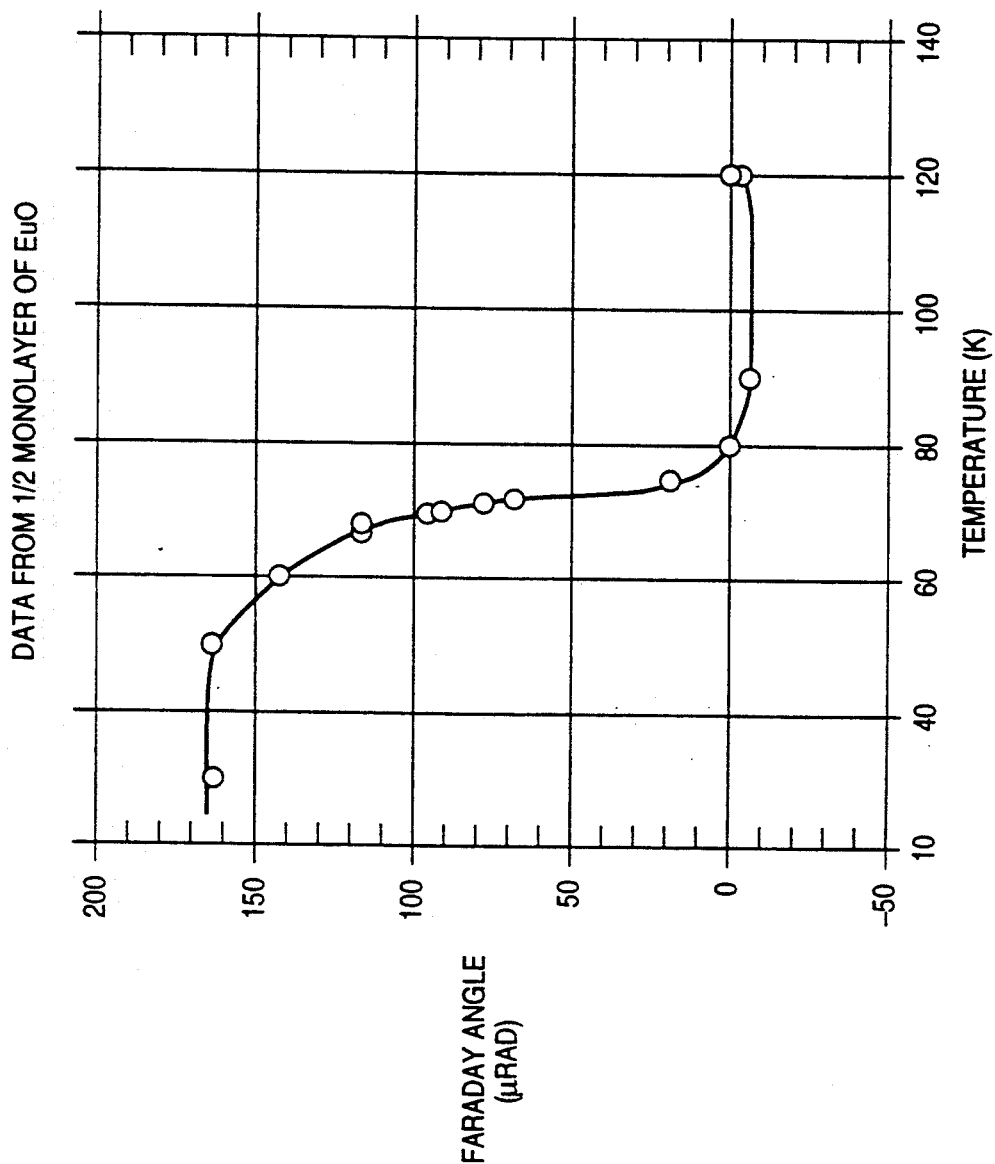
Figure 9C:
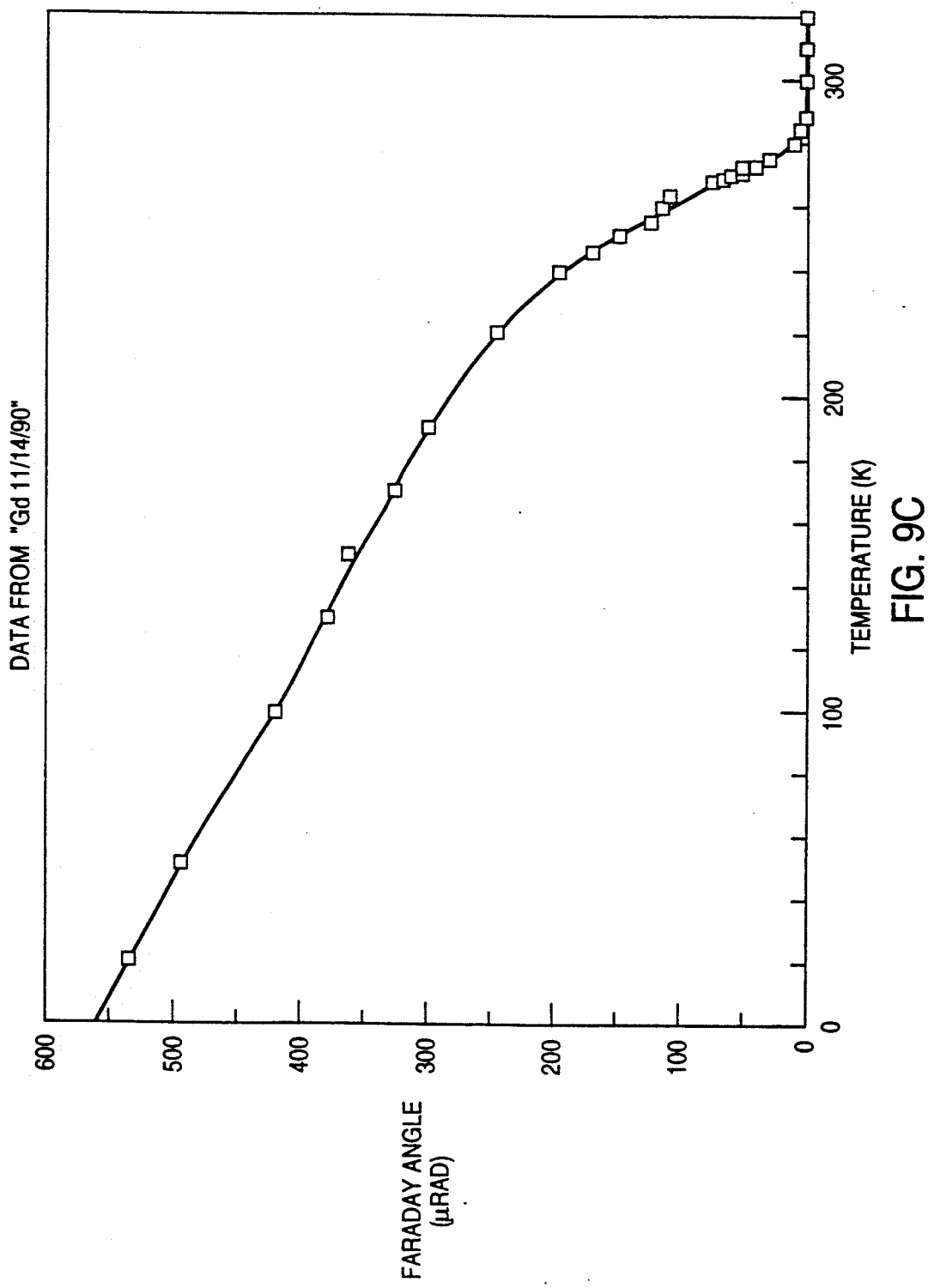

Experimental Results (FIGS. 9A-C)

Several tests confirmed that the apparatus rejects any signals due to reciprocal effects and at the same time is capable of measuring nonreciprocal phase shifts. The following materials served as tests for rejection of reciprocal effects: (1) transmission through a polypropylene sheet of thickness ~0.2 mm exhibiting strong linear birefringence; (2) transmission through an aqueous solution of sucrose (10 g/100 ml), in a cuvette of ~1.5 mm thickness (~1 mrad of reciprocal optical rotation was expected); and (3) reflection from various metallic mirrors. All the above tests showed null results.

The first-harmonic scale factor $k_1 I_0$ can easily be determined by rotating the gyroscope at a known rate or by using a known Faraday material. For the first embodiment of the interferometer, it is convenient to use the 15°/h Earth-rotation rate to generate a calibration signal for the first harmonic. Any changes in the optical power level, which may be more pronounced in this apparatus than when the system is configured solely as a gyroscope, can be determined by monitoring the second-harmonic output. The gyroscope, in the particular configuration, has a constant dc offset of not more than 50 $\mu$rad for the first embodiment and a few $\mu$rad for the second embodiment. This offset, which can vary from day to day (due to variations in the room temperature or the alignment of the fibers), can be zeroed by adding a constant phase shift to the system (e.g., by using the Earth rotation or a Faraday material), or can serve as the reference value for the measurement. In all the measurements the offset was determined at the beginning of the measurement and stayed constant (to within the apparatus sensitivity) throughout the whole measurement including the temperature scan and the x-y translations of the sample.

Although rotation of the gyroscope provides a measurable nonreciprocal effect, additional tests were performed to confirm that the apparatus measures other nonreciprocal effects. The following materials served as tests for detecting nonreciprocal effects: (1) transmission through a 1-mm-thick plate of terbium borosilicate (FR-5) glass with a Verdet constant at 1060 nm of 2.1 $\mu$rad/G-mm (corresponding to a relative phase shift of 4.2 $\mu$rad/G-mm); (2) transmission through a 150-Å film of Eu$_2$O$_3$ (non-magnetic) with a small number of embedded EuO (magnetic) clusters; (3) transmission through a 400-Å film of gadolinium; and (4) reflection from a 400-Å gadolinium film.

FIG. 9A shows typical data for the nonreciprocal phase shift when the FR-5 glass was placed in a magnetic field that was applied along the beam direction (using a solenoid). Note that the direction of the effect reverses appropriately when the magnetic field direction is reversed. The measured phase shifts agree with the tabulated value to within 10%.

FIG. 9B shows a plot of the measured phase shift (twice the Faraday angle) for transmission through the Eu$_2$O$_3$/EuO as a function of temperature. The amount of EuO was determined independently by a SQUID magnetometer scanning from room temperature down to 4K, and was found to be the equivalent of about half a monolayer of pure EuO. A ferromagnetic transition was observed at the expected 69-K transition temperature. The film was placed in the apparatus of FIG. 2 with a field of 30 gauss, and, as can be seen from the plot, showed the ferromagnetic phase transition at 69 K and produced a Faraday effect as expected from the published Verdet constant.

FIG. 9C shows a plot of the measured phase shift on transmission through the gadolinium as a function of temperature (also at 30 gauss). Although the amount of gadolinium was known, it was verified using a SQUID magnetometer. A ferromagnetic transition was observed at the expected 270-K transition temperature. The measured phase shift was also measured for reflection off the same gadolinium film. The apparatus of FIG. 3 was used, but with a field of 100 gauss, and the same ferromagnetic transition was observed.

Applications and Conclusion

In conclusion, it can be seen that the present invention provides an elegant and extremely sensitive technique for measuring nonreciprocal optical effects while rejecting reciprocal effects that may be orders of magnitude larger.

These properties of the invention, and the various features described above make it possible to perform a number of measurements that were formerly difficult or impossible. While the above description shows how to perform magneto-optic microscopy, down to a resolution of a wavelength or even a small fraction of a wavelength, and reports a number of specific measurements, the applications of the invention are far more numerous than initially suggested. For example, it is possible to use the near field capability to probe single domains and investigate domain walls. It is also possible to monitor in real time the deposition of magnetic layers down to monolayer thicknesses, and by depositing a very thin layer of magnetic material, to image the flux lattice of superconductors. While applications in magneto-optic recording seem very natural, the invention can be used in more diverse fields such as evaluating doping in semiconductors by determining carrier density and evaluating spin excitations in molecules to investigate free radicals in biological systems.

While the above is a full description of the preferred embodiments, various modifications, alternative constructions, and equivalents may be used. For example, specific fiber-optic interferometer embodiments are described. However, there are many known configurations for fiber-optic gyroscopes, and at least some of these could presumably be adapted for use with the invention. While a phase modulator is disclosed, a nonreciprocal bias could also be provided by a Faraday rotator subjected to an AC magnetic field, or (for some embodiments) a mechanical dither. Additionally, not all samples need to be cooled, so the illustrated cryostat should be considered optional. Indeed, if it is present, the scanning stage may be located within it. Moreover, other techniques for producing minute apertures, such as covering a pointed transparent body with an opaque film and producing a transparent hole at the tip by cold deformation of the film, could be used instead of the tapered fiber.

Therefore, the above description should not be taken as limiting the scope of the invention which is defined by the claims.

What is claimed is:

1. Apparatus for measuring nonreciprocal optical effects in a sample, comprising:
   a source of light;
   a single-mode filter;
   means for directing light from said source through said single-mode filter to define an input beam;
   means for deriving first and second beams from said input beam;
   means for directing said first and second beams toward the sample, said first and second beams having a definite phase relationship prior to encountering the sample, said first and second beams being circularly polarized at the sample and being related to each other in their direction toward the sample and their handedness at the sample so that a change in the phase relationship provides a measure of nonreciprocal optical effects in the sample;
   means for combining said first and second beams after they have encountered the sample;
   means for passing the resulting combination through the single-mode filter to define a return beam;
   means for subjecting said first and second beams to a time-varying nonreciprocal bias prior to combination; and
   means for measuring the power of the combination after it has passed through the single-mode filter.

2. The apparatus of claim 1 wherein:
   each of said first and second beams passes through the sample once;
   said first and second beams travel in opposite directions toward the sample; and
   said first and second beams are circularly polarized with the same handedness when they encounter the sample.

3. The apparatus of claim 1 wherein:
   said first and second beams are reflected from the sample;
   said first and second beams travel in the same direction toward the sample; and
   said first and second beams are circularly polarized with the opposite handedness when they encounter the sample.

4. The apparatus of claim 1 wherein:
   each of said first and second beams passes through the sample twice;
   said first and second beams travel in the same direction toward the sample; and
   said first and second beams are circularly polarized with the opposite handedness when they encounter the sample.

5. The apparatus of claim 1 wherein said means for deriving comprises:
   means for providing first and second linearly polarized beams having a known initial phase relation at a particular point; and
   means for converting said linearly polarized beams to circularly polarized before they encounter the sample and for converting said circularly polarized beams to linearly polarized after they encounter the sample.

6. The apparatus of claim 1, and further comprising:
   means for focusing said first and second beams on or in the sample; and
   means for effecting relative motion between said first and second beams and the sample.

7. Apparatus for measuring nonreciprocal optical effects in a sample, comprising:
   means defining an optical path;
   means for directing first and second linearly polarized optical beams along said optical path;
   means for combining portions of said first and second beams after they have traveled equal distances along said optical path to define an output beam;
   means for measuring the relative phase of said portions of said output beam;
   means for positioning the sample in said optical path; and
   conversion means, interposed in said optical path, operable to convert linearly polarized light incident thereon to circularly polarized light before the light reaches the sample and further operable to convert circularly polarized light to linearly polarized light after the light leaves the sample;
   whereupon said relative phase provides a measure of the nonreciprocal optical effect of the sample.

8. The apparatus of claim 7 wherein said path defining means comprises a Sagnac interferometer.

9. The apparatus of claim 7 wherein said path defining means comprises a fiber-optic loop.

10. The apparatus of claim 9 wherein said means for directing and said means for combining together comprise first and second directional fiber couplers.

11. The apparatus of claim 7 wherein said means for measuring comprises a detector that provides a detector signal representative of the intensity of light incident thereon.

12. The apparatus of claim 11 wherein said means for measuring further comprises:
   means for modulating the length of said optical path at a given phase modulation frequency; and
   means for measuring a component of said detector signal at a harmonic of said phase modulation frequency.

13. The apparatus of claim 7 wherein:
   each of said first and second beams passes through the sample; and
   said conversion means comprises first and second quarter-wave plates located on opposite sides of the sample.

14. The apparatus of claim 7 wherein:
   each of said first and second beams is reflected from the sample; and
   said conversion means comprises a polarization-selective beam splitter for directing both beams toward the sample and a quarter-wave plate between the beam splitter and the sample.

15. The apparatus of claim 7, and further comprising:
   means, disposed proximate the sample, for limiting the circularly polarized light reaching the sample to a transverse dimension significantly less than the wavelength of the light.

16. The apparatus of claim 15 wherein said means for limiting comprises a tapered optical fiber.

17. In combination with a Sagnac interferometer wherein two linearly polarized beams travel over a common path, the beams having a known relative phase when they commence traveling over the path, apparatus for measuring nonreciprocal optical effects in a sample, comprising:

means for positioning the sample in the path;

conversion means, interposed in the path, for converting linearly polarized light traveling toward the sample to circularly polarized light before it encounters the sample, and for converting circularly polarized light traveling away from the sample to linearly polarized light; and means for measuring the relative phase of the beams after they have traveled over the path;

whereupon a change in the relative phase provides a measure of the non-reciprocal optical effect of the sample.

18. The apparatus of claim 17 wherein:

the path traveled by each of the beams passes through the sample;

the beams travel in opposite directions toward the sample over at least a portion of the path; and the two beams are circularly polarized with the same handedness when they encounter the sample.

19. The apparatus of claim 17 wherein:

each of the beams is reflected by the sample;

the beams travel in the same direction toward the sample over at least a portion of the path; and the two beams are circularly polarized with the opposite handedness when they encounter the sample.

20. Apparatus for measuring nonreciprocal optical effects in a sample, comprising:

means defining an optical path;

means for directing first and second linearly polarized optical beams in opposite directions along said optical path;

means for combining portions of said first and second beams after they have traveled equal geometric distances along said optical path to define an output beam;

means for measuring the relative phase of said first and second beams;

first and second conversion means, interposed in said optical path, each operable to convert linearly polarized light incident thereon to circularly polarized light of a given handedness and each further operable to convert circularly polarized light of said given handedness incident thereon to linearly polarized light; and means for positioning the sample between said first and second conversion means;

whereupon said relative phase provides a measure of the nonreciprocal optical effect of the sample.

21. The apparatus of claim 20 wherein said path defining means comprises a Sagnac interferometer.

22. The apparatus of claim 20 wherein said path defining means comprises a fiber-optic loop.

23. The apparatus of claim 22 wherein said means for directing and said means for combining together comprise first and second directional fiber couplers.

24. The apparatus of claim 20 wherein said means for measuring comprises a detector that provides a detector signal representative of the intensity of light incident thereon.

25. The apparatus of claim 24 wherein said means for measuring further comprises:

means for modulating the length of said optical path at a given phase modulation frequency; and means for measuring a component of said detector signal at a harmonic of said phase modulation frequency.

26. The apparatus of claim 20 wherein at least one of said first and second conversion means comprises a quarterwave plate.

27. A method for measuring nonreciprocal optical effects in a sample, comprising the steps of:

directing first and second circularly polarized light beams toward the sample, the beams having a predetermined phase relationship prior to encountering the sample; and measuring a change in the phase relationship of the beams after they have encountered the sample;

the beams being related to each other in their direction toward the sample and their handedness at the sample so that a change in the phase relationship provides a measure of nonreciprocal optical effects in the sample.

28. The apparatus of claim 27 wherein:

each of the beams passes through the sample once;

the beams travel in opposite directions toward the sample; and the beams are circularly polarized with the same handedness when they encounter the sample.

29. The method of claim 27 wherein:

the beams are reflected from the sample;

the beams travel in the same direction toward the sample; and the beams are circularly polarized with the opposite handedness when they encounter the sample.

30. The method of claim 27 wherein:

each of the beams passes through the sample twice;

the beams travel in the same direction toward the sample; and the beams are circularly polarized with the opposite handedness when they encounter the sample.

31. The apparatus of claim 27 wherein said step of directing comprises the substep of:

providing first and second linearly polarized beams having a known initial phase relation at a particular point; and converting the linearly polarized beams to circularly polarized before they encounter the sample; and converting said circularly polarized beams to linearly polarized after they encounter the sample.

* * * * *